United States Patent [19]

Zupancic et al.

[11] Patent Number: 5,018,380
[45] Date of Patent: May 28, 1991

[54] DIELECTRIC SENSORS

[75] Inventors: Joseph J. Zupancic, Bensenville; Sandra L. Petty-Weeks, West Chicago; Anthony J. Polak, Lake Zurich, all of Ill.

[73] Assignee: Allied-Signal Inc., Morris Township, Morris County, N.J.

[21] Appl. No.: 307,121

[22] Filed: Feb. 6, 1989

[51] Int. Cl.⁵ .............................................. G01N 27/00
[52] U.S. Cl. .................................. 73/23.2; 73/25.03
[58] Field of Search ............................. 73/23, 27 R, 29; 338/35

[56] References Cited

U.S. PATENT DOCUMENTS

| | | | |
|---|---|---|---|
| 4,198,851 | 4/1980 | Janata | 73/23 |
| 4,238,758 | 12/1980 | Suzuki | 357/25 |
| 4,442,422 | 4/1984 | Murata et al. | 338/35 |
| 4,453,126 | 6/1984 | Volgyesi | 324/61 |
| 4,563,893 | 1/1986 | Tanyolac et al. | 73/23 |
| 4,564,882 | 1/1986 | Baxter et al. | 361/286 |
| 4,603,372 | 7/1986 | Abadie et al. | 361/286 |
| 4,627,859 | 12/1986 | Zupancic et al. | 55/158 |
| 4,642,601 | 2/1987 | Sugawara et al. | 338/35 |

Primary Examiner—Hezron E. Williams
Assistant Examiner—Joseph W. Roskos
Attorney, Agent, or Firm—Harold N. Wells; Mary Jo Ryther; Gerhard H. Fuchs

[57] ABSTRACT

The amount of carbon monoxide or oxygen in a gas is measured by determining the change in dielectric properties of a polymer film disposed between two electrodes. A preferred polymer film comprises an organometallic gas carrier interdispersed within an interpenetrating polymer network matrix.

15 Claims, 2 Drawing Sheets

DIELECTRIC SENSORS

This invention relates to detecting and measuring of selected components in gaseous samples. More particularly, it relates to the measurement of oxygen and carbon monoxide in air or other gases.

PRIOR ART

Polymers are generally considered to be nonconductive, but they will carry some electrical current attributed to the migration of ions within the polymer. They exhibit dielectric properties when subjected to an electrical voltage. That is, they carry a current which decreases over a period of time to an equilibrium value. This effect may be attributed to orientation of dipoles in the polymer. A value known as the dielectric constant is commonly measured and is of interest in many electrical applications as an indicator of a material's ability to act as a electrical insulator. Dielectric constant is a term which relates to the relative capacitance of a material compared to air.

Many patents disclose sensors which use the variation in dielectric properties to determine the amount of a particular material which is present. Typically these are humidity sensors, such as those described in the following patents.

In U.S. Pat. No. 4,442,422 a device is disclosed which has the ability to measure humidity in air by the impedance change in a polymer-electrolyte film. An outer film less permeable to water vapor is added to control the deterioration of the responsive under-film.

In U.S. Pat. No. 4,564,882 a humidity sensor is described which measures the effect of changes in moisture on the capacitance of a polymer film. The patent is concerned with forming a structure which provides a rapid response to changes in humidity without being affected by surface contaminants. There is no suggestion of detecting oxygen, carbon monoxide, or any other gases.

A similar device is shown in U.S. Pat. No. 4,603,372. The structure differs from those discussed above in having an outer film serving as an electrode. Humidity is measured by changes in capacitance of a polymer film, but no other gases are indicated to be measurable using this device.

A related sensor is disclosed in U.S. Pat. No. 4,642,601, which is distinguished by using a humidity sensitive layer having hydrophobic particles covered by a hydrophilic outer surface. Such layers are said to be more stable than conventional polymers. Detection of other gases is not suggested.

Metal oxides are also known as measuring elements, for example, in U.S. Pat. No. 4,238,758. Although a metal oxide is used in a semi-conductor transistor to measure hydrogen, it is also suggested that other gases, specifically carbon monoxide and oxygen, can be measured using such metal oxides as $SnO_2$, $ZnO$, and $Fe_2O_3$.

Gas sensors which have included polymer films are disclosed in the following patents for use in quite different applications.

In U.S. Pat. No. 4,453,126 a gas sensor is shown for measuring anesthetic gases. The sensor employs a material between two electrodes and detects the effect on capacitance of absorbing the gas to be measured. An electrical circuit is disclosed to cancel the effect of humidity on the measurement of gas concentration.

A device for detecting odors is disclosed in U.S. Pat. No. 4,563,893 which generally employs a carrier gas to transfer the odor molecules across the dielectric sensor. Means are suggested for removing low molecular weight gases which could interfere with the odor to be measured. Examples include carbon dioxide and nitrogen. There is no suggestion of the use of the device to measure carbon monoxide or oxygen.

A related U.S. Pat. No. , 4,627,859 which is incorporated herein by reference, discloses the use of a particular type of interpenetrating polymer combined with an organometallic gas carrier as a gas enrichment membrane.

Measurement of dielectric constant and impedance properties, which may include both resistive and capacitive elements, is well known in the art. Two types of electrode configurations are commonly used in sensors designed to measure the dielectric or impedance properties of a sensing material, i.e. parallel plate electrodes, often incorporating perforations to increase the mass transport of the sample, and co-planer or parallel plate interdigitated electrodes. The electrode configuration and measurement circuit will depend on the physical properties of the sensing material. An AC signal is usually applied to the material to avoid electrode polarization. The phase angle and amplitude of the resulting signal is then measured and the appropriate calculations, depending on physical properties and device configuration are then made.

SUMMARY OF THE INVENTION

The invention involves a method and apparatus for measuring the amount of carbon monoxide or oxygen in a gas. The gas is brought into contact with a sensing device comprising a film consisting essentially of an organometallic gas carrier dispersed within an interpenetrating polymer network and disposed between two electrodes or deposited on interdigitated electrodes, which are connected with a means for measuring the dielectric properties of the film. The ambient humidity which affects the dielectric properties of the film, is measured and separated from the overall dielectric properties to provide a measure of the carbon monoxide or oxygen in the sample gas.

In one embodiment the interpenetrating polymer network matrix comprises an isocyanate-capped polymer physically entwined with a nitrogen-containing polymer. The organometallic gas carrier preferably is selected from the group consisting of porphyrins, phthalocyanines, derivatives thereof and phosphorus complexes. The metallic portion of the organometallic gas carrier preferably is selected from the group consisting of cobalt, iron, manganese, iridium, and rhodium. The organometallic gas carrier may be about 0.001 to 0.70 wt. percent of the polymer film

DESCRIPTION OF THE PREFERRED EMBODIMENTS

Figure 1:
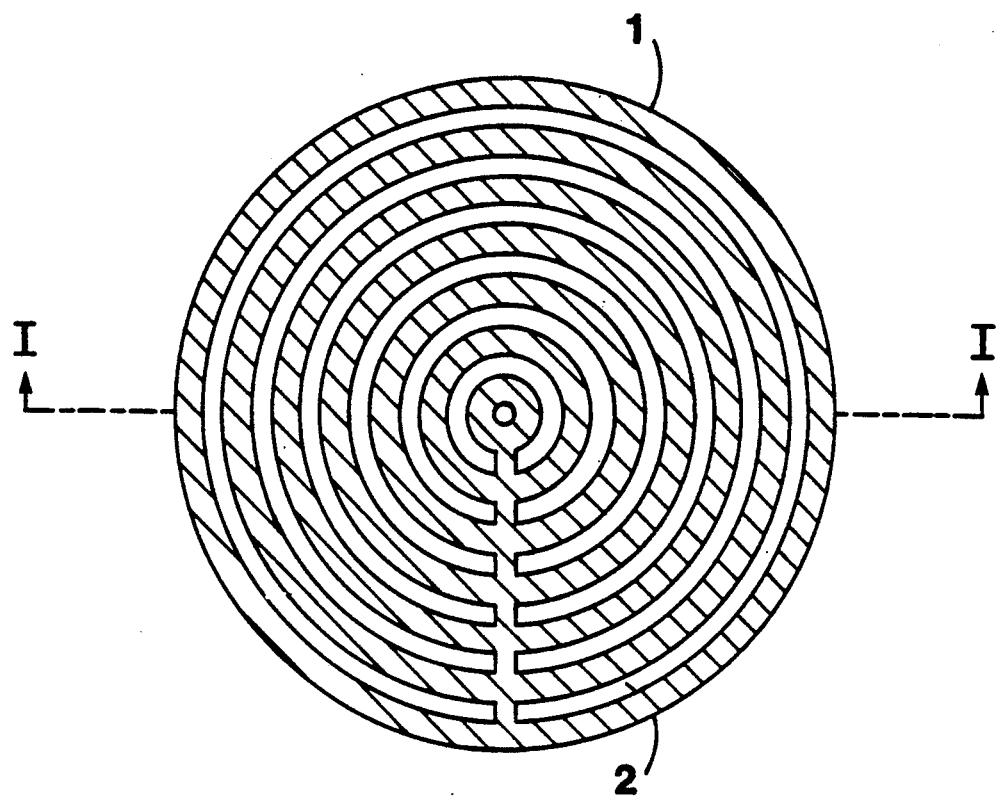
FIG. 1 illustrates a configuration of the instant invention in which the electrode is a perforated plate electrode.

The invention relates to a method and apparatus for measuring the amount of carbon monoxide or oxygen present in a gas as correlated with the change in dielectric properties of a polymer film disposed between two electrodes or deposited on interdigitated electrodes. The composition of such a polymer film has been found to be critical to obtaining the desired performance, that is, not all polymer films are capable of acting as detectors for the presence of carbon monoxide or oxygen, as will be seen. Indeed the interpenetrating polymer networks alone are not suitable, but require the presence of a gas carrier.

POLYMER FILMS

Polymer films according to the invention include an organometallic gas carrier and a polymeric matrix which isolates the particles of the organometallic gas carrier from each other in order to prevent irreversible oxidation or degradation. In addition, the organometallic compound which acts as an oxygen or carbon monoxide carrier must be stable and reversibly react with oxygen or carbon monoxide. The polymeric matrix will comprise an interpenetrating polymer network, consisting of a host polymer and a guest polymer. Such a polymeric network forms flexible and mechanically stable films.

The organometallic compound is used as isolated molecules, the molecules being separated so that no interaction can take place. In addition, the polymeric matrix has an N-ligand present to aid in binding and to assure the reversibility of the action with the particular gas being measured. The presence of this ligand in the polymeric matrix serves to activate and stabilize the organometallic compound which acts as the gas carrier.

The organometallic component will contain a transition metal preferably selected from the group consisting of cobalt, iron, manganese, iridium and rhodium. However, it is also contemplated within the scope of this invention that other transition metals such as zirconium, scandium, yttrium, lanthanum, copper, chromium, vanadium and titanium may also be employed, although not necessarily with equivalent results. The metal is complexed with an organic compound which comprises a porphyrin, phthalocyanine as well as derivatives and phosphorous complexes. Some representative examples of organometallic compounds which may be utilized as one component of the polymeric matrix will include tetraaryl organic complexes such as cobalt tetraphenylporphyrin, cobalt tetratolylporphyrin, cobalt tetraxylylporphyrin, cobalt tetraanisylporphyrin, cobalt tetramesitylporphyrin, cobalt tetra (chlorophenyl)porphyrin, cobalt tetra(bromophenyl)porphyrin, cobalt tetranitroporphyrin, cobalt tetracyanoporphyrin, iron tetraphenylporphyrin, iron tetratolylporphyrin, iron tetraxylylporphyrin, iron tetraanisylporphyrin, iron tetramesitylporphyrin, iron tetra(chlorophenyl)porphyrin, iron tetra(bromophenyl)porphyrin, iron tetranitroporphyrin, iron tetracyanoporphyrin, manganese tetraphenylporphyrin, manganese tetratolylporphyrin, manganese tetraxylylporphyrin, manganese tetraanisylporphyrin, manganese tetramesitylporphyrin, manganese tetra(chlorophenyl)porphyrin, manganese tetra(bromophenyl)porphyrin, cobalt phthalocyanine monosulfonate, cobalt phthalocyanine disulfonate, cobalt phthalocyanine trisulfonate, cobalt phthalocyanine tetrasulfonate, cobalt phthalocyanine monocarboxylate, cobalt phthalocyanine dicarboxylate, cobalt phthalocyanine tricarboxylate, cobalt phthalocyanine tetracarboxylate, tetrapropyl phthalocyanine, cobalt monochloro phthalocyanine, cobalt dichloro phthalocyanine, cobalt trichloro phthalocyanine, cobalt tetrachloro phthalocyanine, cobalt monobromo phthalocyanine, cobalt tribromo phthalocyanine, cobalt diiodo phthalocyanine, cobalt tetraiodo phthalocyanine, iron phthalocyanine monosulfonate, manganese phthalocyanine dicarboxylate, iron phthalocyanine tricarboxylate, manganese phthalocyanine tetracarboxylate, iron tetramethyl phthalocyanine, manganese tetraethyl phthalocyanine, iron tetrapropyl phthalocyanine, manganese monochloro phthalocyanine, iron dichloro phthalocyanine, manganese trichloro phthalocyanine, iron tetrachloro phthalocyanine, manganese monobromo phthalocyanine, iron tribromo phthalocyanine, manganese diiodo phthalocyanine, iron tetraiodo phthalocyanine, Bis[bis(diphenylphosphino)ethane]rhodium, Bis[bis(diphenylphosphino)ethane]iridium, chloro-carbonyl-bis(triphenyl phosphine)iridium, chloro-carbonyl-bis(triphenylphosphine)rhodium, and the like.

The other component of the polymer matrix, which provides a medium for the organometallic complex comprises an interpenetrating polymer network. This interpenetrating network which provides the matrix for the organometallic complex must be hydrophobic and nonacidic in character as well as possessing a low dielectric constant. The interpenetrating polymeric network must also possess a nitrogen ligand which serves both to stabilize and activate the organometallic complex. In addition, the matrix must also isolate the particles of the organometallic complex. An interpenetrating polymeric network comprises a host polymer and a guest polymer. It is distinguished from similar blends of two or more polymers in that at least one of the polymer components of the interpenetrating network is crosslinked to itself or to like components, but not to the other polymer or polymers. This unique crosslinking which is inherent to an interpenetrating polymer network system means that the polymers which comprise the components of the system are physically entangled or entwined but are not bound to one another by chemical bonds. For example, other polymer systems provide a chemical crosslinking or covalent bonding between the different types of polymer chains. In the preferred embodiment of the present invention, the host polymer comprises a nitrogen-containing compound and preferably a heterocyclic nitrogen-containing compound. Some representative examples of these host polymers are poly(2-vinylpyridine), poly(4-vinylpyridine), derivatives of poly(4-vinylpyridine) such as the cyano-, amino-, and alkyl moieties containing from 1 to 4 carbon atoms such as poly(2-cyano-4-vinylpyridine), poly(2-amino-4-vinylpyridine), poly(2-methyl-4-vinylpyridine), poly(2-ethyl-4-vinylpyridine), poly(2-propyl-4-vinylpyridine), poly(2-butyl-4-vinylpyridine), poly(N-vinylimidazole), poly(benzimidazole), poly(N-vinyl-2-methylimidazole), poly(vinyl-benzimidazole), imidazole-modified polyethyleneimine, imidazole-modified epiamine, poly(4-vinylpyridine-acrylonitrile), poly(4-vinylpyridine-styrene), poly(4-vinyl-pyridine-vinyltoluene), poly(N-vinylimidazole-styrene), poly(N-vinylimidazole-vinyl(toluene), poly(N-vinylimidazole-N-vinylpyrrolidine), poly(N-vinyl-2-methylimidazole-styrene), poly(N-vinyl-2-methylimidazole-vinyl toluene), and poly(N-vinyl-2-methylimidazole-N-vinylpyrrolidinone).

The guest polymer which forms the other component of the interpenetrating polymer network comprises an isocyanate-capped polymer such as poly[methylene poly(phenylisocyanate)], polymers prepared by reacting a polyglycol such as polyethylene glycol, polypropylene glycol or block copolymers containing both ethylene glycol and propylene glycol with an isocyanate containing compound such as toluenediisocyanate, methylenediphenylisocyanate, ethylenediphenylisocyanate, propylenediphenylisocyanate, and the like.

The guest polymer may also be derived from cyclic siloxanes such as octamethylcyclotetrasiloxane, tetramethyltetraphenylcyclotetrasiloxane, hexamethylcyclotrisiloxane, trimethyltriphenylcyclotrisiloxane, tetramethyltetraethylcyclotetrasiloxane, trimethyltriethylcyclotrisiloxane, octaethylcyclotetrasiloxane, hexaethylcyclotrisiloxane, octaphenylcyclotetrasiloxane, hexaphenylcyclotrisiloxane, and the like.

While the host polymers and the guest polymers in the interpenetrating polymer network discussed above are preferred examples they are only representative of the type of compounds which may be employed and it is not intended to exclude other combinations which provide useful detectors.

The formation of the isocyanate-capped polymer by reacting an isocyanate-containing compound with a polyol is usually carried out at reaction conditions which include an elevated temperature in the range of from about 50° to about 100° C. and preferably at atmospheric pressure, although superatmospheric pressures ranging from 2 to about 50 atmospheres may be employed. The average molecular weight of the isocyanate-capped polymer can be varied by utilizing varying molecular weight polyols, block copolymers or capping agents. For example, one particular type of block copolymer of ethylene glycol and propylene glycol which may be employed comprises the polymer which contains about 20% ethylene glycol and about 80% propylene glycol, the block copolymer having a molecular weight of about 2750. Other copolymers containing varied amounts of ethylene glycol and propylene glycol as well as varying molecular weights may also be employed. In the preferred embodiment of the invention, the reaction is carried out in the absence of a solvent although solvents such as chloroform, carbon tetrachloride, or other organic solvents in which the compounds are soluble may also be employed.

When preparing the interpenetrating network the two polymers, which have been designated as the host polymer and the guest polymer, are dissolved in a mutually compatible solvent. When the two solutions are admixed, the chains of polymers become entwined. To prepare the polymer film the organometallic gas carrier is added to the solution and cast upon a support electrode or porous backing support material. As the solvent evaporates, the chains of the component polymers remain physically entwined. Inasmuch as this is only a physical interaction, it differs from prior polymeric membranes in that no chemical crosslinking or covalent bonding has taken place between the different types of polymer chains. After casting and evaporation of the solvent, the composite is then cured in the presence of water vapor. A portion of the isocyanate-capped polymer which, in this system, comprises the guest polymer will hydrolyze to form an amine-capped polymer. This portion of the amine-capped polymer will react with the remaining portion of the original isocyanate-capped polymer to form a cross-linked network which physically and permanently entwines or entangles the nitrogen-containing compound in the network. However, the nitrogen-containing compound which comprises the host polymer is neither chemically bonded nor cross-linked either to itself or to the polyurea polymer which results from the reaction of amine-capped polymer with isocyanate-capped polymer. Inasmuch as the nitrogen-containing compound or polymer is so entwined or entangled in the cross-linked polyurea polymer, it is no longer soluble and cannot be dissolved out of the interpenetrating network matrix, thus resulting in a polymeric membrane system which will remain physically stable during its use in a detector for carbon monoxide or oxygen.

In a similar fashion to that described above for interpenetrating polymer networks based on isocyanate-capped polymers the cyclic siloxanes generate a guest polymer network, except the mode of reaction is different. The cyclic siloxanes are cured via a base catalyzed reaction in which the cyclic siloxane undergoes ring opening and polymerization. The catalyst in this system can be an alkali hydroxide or silanolate, quatanary ammonium hydroxide or silanolate. Examples include sodium hydroxide, potassium hydroxide, sodium trimethylsilanoate, potassium trimethylsilanoate, tetramethylammonium hydroxide, tetrabutylammonium hydroxide, tetramethylammonium trimethylsilanoate, tetrabutylammonium trimethylsilanoate, etc. The resulting guest polymer is a polysiloxane or silicone, crosslinking can be introduced by the incorporation of a bifunctional or multifunctional monomer which co-polymerizes with the cyclosiloxane.

The formation of the polymer film may be affected at operating conditions which include ambient temperature and atmospheric pressure. The choice of solvent which is to be employed in preparing the membrane composite will depend upon various factors. For example, the solvent must be capable of dissolving the host polymer and the guest polymer as well as the organometallic gas carrier. After thoroughly admixing the host polymer comprising the nitrogen-containing compound, the resulting solution is then purged with an inert gas such as nitrogen. The organometallic compound may be added and mixed until a complete solution is obtained. Thereafter, the guest polymer which is also dissolved in the solvent is admixed with the solution of host polymer and organometallic compound in predetermined amounts so that the resulting casting solution will contain the host polymer, guest polymer and organometallic compound in the desired proportions. An example of an appropriate solvent which may be employed in this process comprises nitromethane, although other solvents such as benzene, toluene, chloronitromethane, butyrolactone, methylpropylsulfone, and the like, mixed solvent systems such as nitromethane-methanol, nitromethane-ethanol, nitromethane-isopropanol, may also be employed. In the preferred embodiment of the invention, the host polymer comprising the nitrogen-containing compound will be present in the casting solution in an amount in the range of from about 0.10% to about 5.00% by weight; the guest polymer comprising the isocyanate-capped polymer will be present in an amount in the range of from about 0.10% to 5.00% by weight and the organometallic compound comprising the gas carrier will be present in an amount in the range of from about 0.001% to about 0.70% by weight.

The polymer film may be deposited by contacting an interdigitated electrode with the casting solution. The thickness of the film may be controlled by the concentration of the polymer network in the solution and the rate of withdrawal of the support material from the solution.

The resulting film is cured by exposure to a hydrous atmosphere in a curing zone. The curing is carried out at a temperature in the range of from about ambient (20°-25° C.) up to about 100° C. while maintaining the atmosphere in the curing zone at a relative humidity which will range from about 0% to about 100%. The curing of the membrane requires from about five minutes to about 48 hours, the time of curing being dependent upon the various parameters such as temperature and humidity. In any instance, the time will be sufficient to generate a substituted amine thereby converting a portion of the isocyanate-capped polymer to an amine-capped polymer. As was hereinbefore set forth, the remaining portion of the isocyanate-capped polymer will react with the amine-capped polymer to form a reaction product comprising a crosslinked network, physically and permanently entwining the host polymer comprising the heterocyclic nitrogencontaining compound in said network. This film can then be passed. if so desired, through a second cure with a relative humidity of 0% at temperature in the range of ambient (20°-25° C.) to 100° C., for period of five minutes to 48 hours.

Measurement of the dielectric properties of the polymer film described could be made in any device in which the polymer was disposed between two electrodes. Practically, such measurements are conveniently made with thin metal film interdigitated electrodes disposed on a substrate and having the polymer film covering the electrodes. Such electrodes are available commercially but of course could be prepared especially for this use. Dielectric measurements are made to monitor the curing of polymers in industrial applications and consequently the use of such equipment in preparing sensors of the invention and measuring the presence of carbon monoxide or oxygen is convenient. As shown in the examples, a polymer matrix of the invention may be deposited on an integrated circuit sensor intended for use in monitoring polymerization and then using the modified sensor as a gas detecting device.

In general, the sensor is exposed to the sample gas and a low frequency alternating voltage is applied to one electrode. The voltage induced at the second electrode is reduced in amplitude and phase shifted. These changes can be related to the dielectric loss factor and the ionic conductivity. These values are affected by the presence of carbon monoxide or oxygen and thus the instrument can be calibrated to provide the concentration of carbon monoxide or oxygen present. Humidity also affects the dielectric properties and its effect must be measured and subtracted to obtain the correct value for carbon monoxide or oxygen.

The polymer film when employed with the incorporation of the organometallic gas carrier will display a sensitivity to humidity. Water, water vapor or humidity does not deteriorate its performance, however it does change the response due to overlapping response of the polymer—water dielectric properties. Therefore, it is necessary to employ a companion or compensating sensor which measures the humidity or water vapor. This sensor can be employed in an electrical package which directly compensates for the difference in response for humidity or water changes in the carbon monoxide or oxygen sensor. Ideally, the humidity or water vapor sensor would match the response of the carbon monoxide or oxygen sensor to humidity or water vapor changes. This can best be achieved by employing the interpenetrating polymer network utilized in the carbon monoxide or oxygen sensor without the organometallic gas carrier. By utilizing this approach, both sensors will respond in a matched or equivalent fashion to water vapor or humidity, there will be no mismatch due to diffusion constant, solubility or diffusivity for water in the polymer system.

FIGS. 1-4 illustrate specific embodiments of the invention of the instant application. FIG. 1 illustrates a configuration in which one of the electrodes is in the form of a perforated plate electrode. Reference numeral 1 indicates one of the rings of the perforated plate electrode. The electrode is laid over polymeric matrix 2 which contains the organometallic gas carrier.

Figure 2:
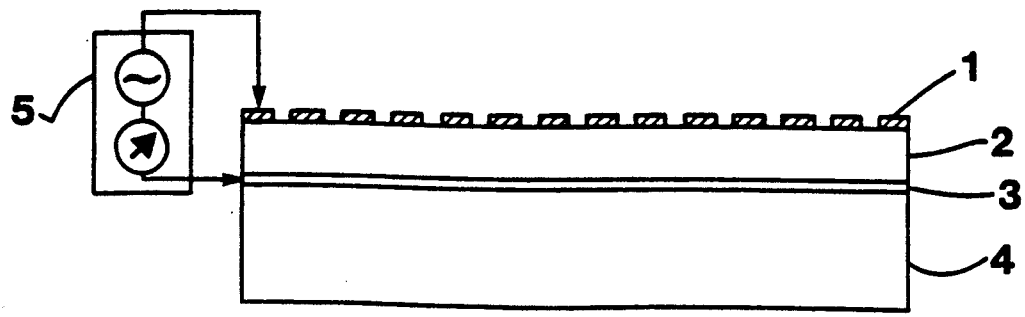
FIG. 2 is a sectional view taken on line I—I through the perforated plate electrode of FIG. 1.

FIG. 2 is sectional view taken on line I—I through the perforated plate electrode of FIG. 1. Reference numeral 1 indicates one of the ring of the perforated plate electrode. The electrode is laid over polymeric matrix 2 which contains the organometalilc gas carrier. Below the polymeric matrix is a second electrode, parallel plate electrode 3, and, beneath the electrode, support medium 4. An AC capacitance/impedance bridge 5 shown schematically illustrates a means for measuring the dielectric properties of the polymer film.

Figure 3:
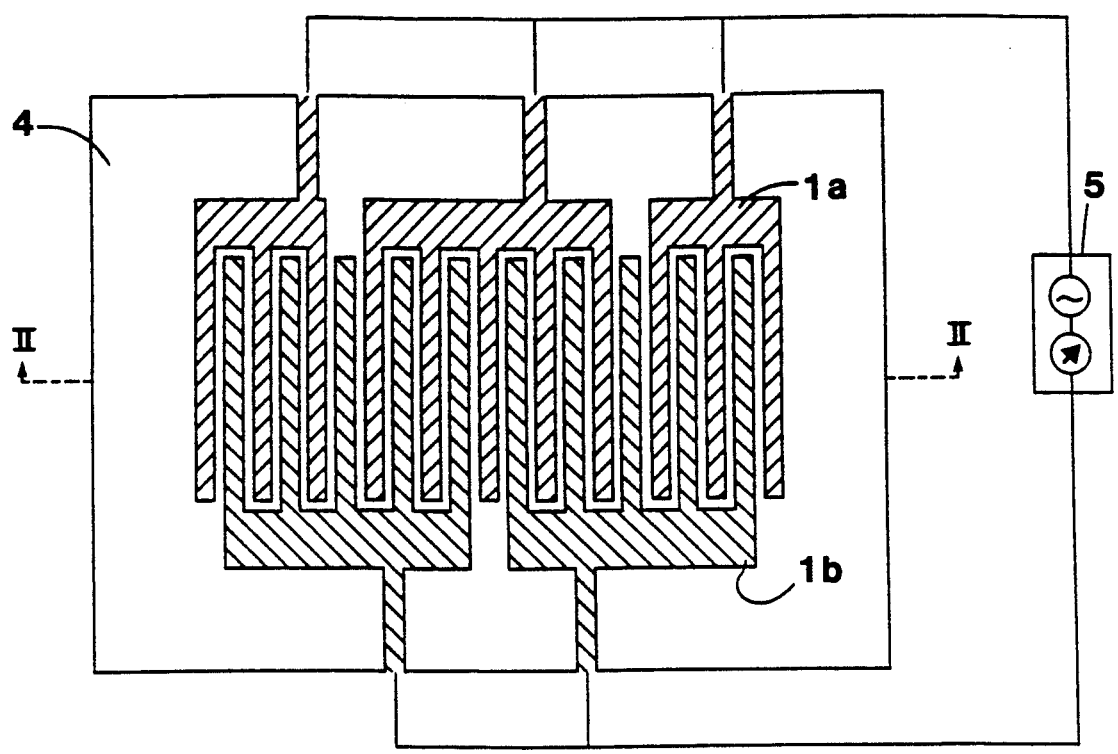
FIG. 3 illustrates a configuration of the instant invention in which the electrode is an interdigitated electrode.

FIG. 3 illustrates a configuration of the instant invention which uses interdigitated electrodes. Reference numerals 1a and 1b indicate the interdigitated electrodes which are laid over support medium 4. Polymeric matrix 2 is laid over both the electrodes and the support medium and is not evident from this drawing (see FIG. 4). An AC capacitance/impedance bridge 5 shown schematically illustrates a means for measuring the dielectric properties of the polymer film.

Figure 4:
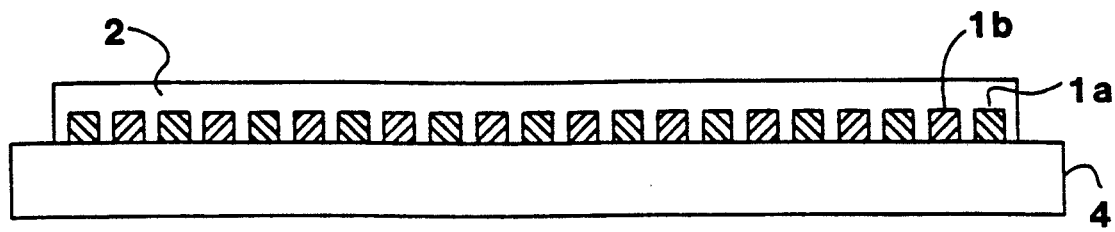
FIG. 4 is sectional view taken on line II—II through the interdigitated electrode of FIG. 3.

FIG. 4 is sectional view taken on line II—II through the interdigitated electrode of FIG. 3. Reference numerals 1a and 1b indicate the interdigitated electrodes covered by polymeric matrix 2. Polymer matrix 2 contains the organometallic gas carrier. Below polymer matrix 2 is support medium 4.

EXAMPLE 1

Preparation of poly(N-vinylimidazole-N-vinyl pyrrolidinone) [P(NVI-VP)]

P(NVI-VP) was prepared by charging 1.4 gm of potassium persulfate and 450 ml of water into a 1 liter 3-neck round bottom flask equipped with an addition funnel, mechanical stirrer, condenser, thermometer, and nitrogen purge. The solution was stirred for 30 minutes while being purged with nitrogen and thereafter heated to 60° C. A mixture of 55 gms (0.5 mols) of N-vinylpyrrolidinone (VP) and 47 gms (0.5 mols) of N-vinylimidazole (NVI) was added over 1.25 hours. The reaction temperature was increased to 85° C. for 2 hours, then the mixture was allowed to cool to 25° C. and 1.0 gm. of azoisobutyronitrile (AIBN) was added. The mixture was then reheated to 85° C. and held there for 1 hour before cooling to 25° C. The polymer was precipitated by addition of 1,4 dioxane. After filtering, the polymer was dried overnight under vacuum at 60°

C. The yield was 53.6 g of polymer (52.5%), $n_{inh}$ (EtOH, 30° C.)=0.885. The elemental analysis was 62.93% C, 7.31% H, 20.23% N, C/N=3.11. The polymer was calculated to be 47.1 mol.% NVI and 52.9 mol.% VP.

EXAMPLE 2

Comparative

Poly(N-vinylimidazole-N-vinylpyrrolidinone-Poly[methylene poly(phenylisocyanate)] Dielectric Sensor A sensor was prepared by coating a dielectric sensor with interdigitated electrodes of copper supplied by Micromet, Cambridge, Mass. with a solution containing 0.4 wt.% poly(N-vinylimidazole-N-vinyl-pyrrolidinone) [P(NVI-VP)] of Example 1 and 0.6 wt.% poly[methylene poly(phenylisocyanate)] [PMDI] in nitromethane. After air drying for 30 minutes, the film was cured at 50° C. in air having a relative humidity of 93% for 18 hours, followed by a 3 hour cure at 70° C. and at 0% relative humidity A second coat was applied and cured under substantially the same conditions. The sensor was then ready to be tested.

EXAMPLE 3

Poly(N-vinylimidazole-N-vinylpyrrolidinone)-Poly[methylene poly(phenylisocyanate)]-Co(II) tetra (p-anisole) porhydrin Dielectric Sensor Another sensor was prepared as in Example 2 except that 0.0372 wt.% cobalt(II) tetra (p-anisole) porphyrin [Co(II)TAP] was added to the nitromethane solution.

EXAMPLE 4

The sensors prepared in Examples 2 and 3 were exposed to dry air (i.e., about 20% $O_2$) for one hour, then to dry nitrogen, and finally to dry air again. The permittivity ($\epsilon'$) and loss factor ($\epsilon''$) were measured at 0.01 Hz using a Eumetric TM System II Microdielectrometer supplied by Micromet, Cambridge, Mass. The dielectric properties measured as summarized in the following table:

TABLE A

| Atmosphere | Example 2 | Example 3 |
|---|---|---|
| Dry Air | $\epsilon' = 2.0$ | $\epsilon' = 2.0$ |
|  | $\epsilon'' = 0.026 \pm 0.002$ | $\epsilon'' = 0.039 \pm 0.002$ |
| Dry $N_2$ | $\epsilon' = 2.0$ | $\epsilon' = 2.1$ |
|  | $\epsilon'' = 0.024 \pm 0.003$ | $\epsilon'' = 0.086 \pm 0.006$ |
| Dry Air | $\epsilon'' = 2.0$ | $\epsilon' = 2.0$ |
|  | $\epsilon'' = 0.026 \pm 0.003$ | $\epsilon'' = 0.044 \pm 0.004$ |

It can be seen that the sensor of Example 2, which contained no organometallic compound was unable to detect the presence of oxygen relative to nitrogen. The sensor of Example 3 showed a distinct change in dielectric properties when no oxygen was present, indicating its potential for use as a oxygen detector.

EXAMPLE 5

Two sensors were prepared according to Examples 2 and 3, thus providing a sample which is not responsive to oxygen (a) and another which is responsive to the oxygen content of a gas (b). The first sample was exposed to dry air and to air having 28% relative humidity and the dielectric properties measured at 0.01 Hz.

TABLE B

| Atmosphere | Sample (a) | Sample (b) |
|---|---|---|
| Dry Air | $\epsilon' = 2.15$ | $\epsilon' = 2.02$ |
|  | $\epsilon'' = 0.06$ | $\epsilon'' = 0.04$ |
| Air with 28% R.H. | $\epsilon' = 2.52$ | $\epsilon' = 2.34$ |
|  | $\epsilon'' = 0.23$ | $\epsilon'' = 0.24$ |

It will be evident that the sensor responds to the presence of water in the air and thus could be used as a humidity sensor. However, since many gases will contain moisture, such a response will be seen when oxygen is to be detected according to the invention. Thus, a sensor such as sample (a), which is not sensitive to oxygen, would be employed as a reference against which the sensor is sensitive to oxygen (and humidity as well) is compared. That is the difference in electrical measurements will be related to the amount of oxygen present in the sample gas.

EXAMPLE 6

Comparative

Poly(4-Vinylpyridine)-Co(II) Tetra (p-anisole) porphyrin dielectric sensor

A 1.00 wt.% solution of poly(4-vinylpyridine) was prepared in nitromethane. Co(II)TAP was added to this solution to form a ratio of 1:100 Co(II)TAP:vinylpyridine, the undissolved Co(II)TAP was filtered off and the resulting solution was cast onto an interdigitated Micromet sensor. This sensor showed no significant change in dielectric properties when exposed to a nitrogen atmosphere or pure oxygen atmosphere.

EXAMPLE 7

Comparative

Silicon Rubber-Co(II) Tetra (p-anisole) porphyrin dielectric sensor

A 1.00 wt.% solution of silicone rubber (Sylgard 186—Dow Corning) in dichloromethane containing 0.001 wt.% of Co(II)TAP was cast onto an interdigitated Micromet sensor and the resulting film was cured for 3 hours at 80° C. This sensor showed no significant change in dielectric properties when exposed to a nitrogen atmosphere of pure oxygen atmosphere.

EXAMPLE 8

The sensor 3 is utilized in the detection of carbon monoxide in a manner similar to that shown in Example 4 for the detection of oxygen. The sensor is exposed to an atmosphere containing carbon monoxide and the dielectric properties (permittivity and loss factor) changes at frequencies of 0.005 and 0.01 Hz monitored.

What is claimed is:

1. A method of measuring the amount of carbon monoxide or oxygen in a gas comprising:
   (a) contacting said gas with a film consisting essentially of an organometallic gas carrier dispersed within an interpenetrating polymer network in contact with electrodes having a means for measuring the dielectric properties of said polymer film;
   (b) measuring the dielectric properties of said polymer film; and,
   (c) correlating the measured dielectric properties with the amount of carbon monoxide or oxygen present in said gas.

2. The method of claim 1 wherein the effect of ambient humidity on the dielectric properties of said polymer is measured and separated from the dielectric properties measured in (b).

3. The method of claim 2 wherein said interpenetrating polymer network matrix comprises (1) an isocyanate-capped polymer physically entwined with (2) a nitrogen-containing polymer.

4. The method of claim 1 wherein said organometallic gas carrier comprises an organic compound selected from the group consisting of porphyrins, phthalocyanines, derivatives thereof, and phosphorus complexes.

5. The method of claim 4 wherein the metallic portion of said organometallic gas carrier is selected from the group consisting of cobalt, iron, manganese, iridium, and rhodium.

6. The method of claim 5 wherein the metallic portion of said organometallic gas carrier is cobalt.

7. The method of claim 1 wherein said organometallic gas carrier is 0.001 to 0.70 wt. percent of said polymer film.

8. The method of claim 1 wherein the electrodes are interdigitated electrodes.

9. A sensor for detecting and measuring the amount of carbon monoxide or oxygen in a gas comprising:
  (a) a polymer film disposed in a porous support, said film comprising an organometallic gas carrier dispersed within an interpenetrating polymer network;
  (b) two electrodes in contact with the polymer film;
  (c) means for measuring the dielectric properties of said polymer film of (a) between said electrodes of (b);
  (d) means for correlating the measured dielectric properties with the amount of carbon monoxide or oxygen present in said gas.

10. The sensor of claim 9 wherein said interpenetrating polymer network comprises: (1) an isocyanate-capped polymer physically entwined with (2) a nitrogen-containing polymer.

11. The sensor of claim 9 wherein said organometallic gas carrier comprises an organic compound selected from the group consisting of porphyrins, phthalocyanines, derivatives thereof, and phosphorous complexes.

12. The sensor of claim 9 wherein the metallic portion of said organometallic gas carrier is selected from the group consisting of cobalt, iron, manganese, iridium, and rhodium.

13. The sensor of claim 12 wherein the metallic portion of said organometallic gas carrier is cobalt.

14. The sensor of claim 9 wherein said organometallic gas sensor is 0.001 to 0.70 wt. percent of said polymer film.

15. The sensor of claim 9 wherein the electrodes are interdigitated electrodes.

* * * * *